US012485044B2

(12) United States Patent
Östan et al.

(10) Patent No.: US 12,485,044 B2
(45) Date of Patent: Dec. 2, 2025

(54) WOUND DRESSING

(71) Applicant: MÖLNLYCKE HEALTH CARE AB, Gothenburg (SE)

(72) Inventors: Karin Östan, Nödinge (SE); Erik Båtelson, Västra Frölunda (SE)

(73) Assignee: Mölnlycke Health Care AB, Mölndal (SE)

( * ) Notice: Subject to any disclaimer, the term of this patent is extended or adjusted under 35 U.S.C. 154(b) by 681 days.

(21) Appl. No.: 17/277,609

(22) PCT Filed: Sep. 16, 2019

(86) PCT No.: PCT/EP2019/074735

§ 371 (c)(1),
(2) Date: Mar. 18, 2021

(87) PCT Pub. No.: WO2020/064406

PCT Pub. Date: Apr. 2, 2020

(65) Prior Publication Data

US 2022/0031521 A1 Feb. 3, 2022

(30) Foreign Application Priority Data

Sep. 25, 2018 (EP) .................................... 18196670

(51) Int. Cl.
*A61F 13/02* (2024.01)
*A61F 13/00* (2024.01)
*A61F 13/0246* (2024.01)

(52) U.S. Cl.
CPC .... *A61F 13/0259* (2013.01); *A61F 13/00059* (2013.01); *A61F 13/0253* (2013.01)

(58) Field of Classification Search
CPC .... A61F 13/00; A61F 13/02; A61F 13/00085; A61F 13/60; A61F 13/0259; A61F 13/00059; A61F 13/0008; A61F 13/0253; A61F 13/0266; A61F 13/0246; A61F 2013/00238; A61F 2013/00246; A61F 2013/00251; A61F 2013/00255; A61F 2013/00582; A61F 5/443
USPC ................ 602/43, 44, 47, 52, 54, 57, 58, 59
See application file for complete search history.

(56) References Cited

U.S. PATENT DOCUMENTS 4,334,530 A * 6/1982 Hassell ............... A61F 13/0203 602/42
10,086,107 B2 10/2018 Cotton
2010/0159192 A1 6/2010 Cotton
2016/0030250 A1 2/2016 Caneppele et al.
(Continued)

FOREIGN PATENT DOCUMENTS

CN 205515888 U 8/2016
KR 20040027941 A * 4/2004
(Continued)

OTHER PUBLICATIONS

KR 20040027941 A machine translation (Year: 2004).*
(Continued)

*Primary Examiner* — Caitlin A Carreiro
(74) *Attorney, Agent, or Firm* — Ballard Spahr LLP

(57) ABSTRACT

The present disclosure generally relates to a wound dressing for a wound, specifically adapted for reducing the risk of disturbance of the wound when removing the wound dressing. The present disclosure also relates to a wound treatment method.

17 Claims, 6 Drawing Sheets

(56) References Cited

U.S. PATENT DOCUMENTS

| | | | | |
|---|---|---|---|---|
| 2016/0193086 | A1* | 7/2016 | Castle | A61F 13/00987 156/247 |
| 2017/0252221 | A1 | 9/2017 | Scopelliti | |

FOREIGN PATENT DOCUMENTS

| | | | | | |
|---|---|---|---|---|---|
| WO | WO-9307841 | A1 | * | 4/1993 | A61F 13/0213 |
| WO | WO-0019948 | A1 | * | 4/2000 | A61F 13/00059 |
| WO | WO-2007113597 | A2 | * | 10/2007 | A61F 13/0213 |
| WO | WO-2008034897 | A1 | * | 3/2008 | A61F 13/0203 |
| WO | WO-2012143665 | A1 | * | 10/2012 | A61F 13/00068 |
| WO | WO-2017127369 | A1 | * | 7/2017 | A61F 13/00063 |

OTHER PUBLICATIONS

CN 201980057153.0, "First Office Action", Sep. 24, 2021, 10 pages.

CN 201980057153.0, "Second Office Action", issued Jun. 10, 2022, 10 pages (including English translation).

LeBlanc et al., "The Art of Dressing Selection: a Consensus Statement on Skin Tears and Best Practice", Advances in Skin & Wound Care, vol. 29, No. 1, pp. 32-46 (2015).

Skin tears Standardised care process, pp. 1-6 (2018).

* cited by examiner

WOUND DRESSING

CROSS-REFERENCE TO RELATED APPLICATIONS

This application is a U.S. National Phase of International Application No. PCT/EP2019/074735, filed Sep. 16, 2019, which claims the benefit of European Application No. 18196670.6, filed Sep. 25, 2018, the entire contents and disclosures of which are incorporated herein by reference.

TECHNICAL FIELD

The present disclosure generally relates to a wound dressing for a wound, specifically adapted for reducing the risk of disturbance of the wound when removing the wound dressing. The present disclosure also relates to a wound treatment method.

BACKGROUND

The treatment of wounds with dressings involves a wide variety of situations and applications. A corresponding variety of different types of dressings are available for treating wounds. Each type of wound undergoes several stages of healing and may require different modes of treatment depending on the stage of healing. Thus, the treatment of a wound involves the selection of a dressing based on the particular type of wound and the various healing stages that are contemplated. Considerations such as size, location, etc. also play a role in selecting a dressing.

However, regardless of the various considerations, the treatment of wounds necessarily involves the periodic changing of the dressings being used to treat the wound. The problem attendant with changing dressings is that the wound is often disturbed during the removal of the dressings, resulting in pain and an extended healing time. The risk of such wound damage requires extensive nursing time to remove and replace dressings with various techniques to help reduce the wound damage and pain.

Generally, as for example is exemplified in WO2017127369A1, this is solved by reducing the adherence between the wound and the wound dressing. In WO2017127369A1 the presented wound dressing product is arranged to comprise a tacky silicone coating that is provided for reducing the above-mentioned adherence between the wound and the wound dressing.

Even though the solution proposed in WO2017127369A1 shows some improvements to the reducing risk for wound damage and pain, some situations exist where reduced adherence is not enough for wound damage avoidance. With the above in mind, there appears to be room for further improvements for reducing the risk of wound damage and pain for a patient when removing a wound dressing.

SUMMARY

According to an aspect of the present disclosure, it is therefore provided a wound dressing, comprising a substrate having an upper surface and a lower surface, a wound facing layer arranged at the lower surface of the substrate, a first release sheet releasibly covering and protecting a first portion the wound facing layer, and a second release sheet releasibly covering and protecting a second portion of the wound facing layer, wherein the second portion of the wound facing layer is non-overlapping with the first portion of the wound facing layer, wherein an interface between the first and the second release sheet defines an overall interface direction, a printed or dyed instruction comprising a direction of removal of the wound dressing is visibly arranged at an upward facing side of the wound dressing, the upward facing side of the wound dressing arranged at the same side of the substrate as the upper surface of the substrate, and the direction of the removal of the wound dressing is essentially perpendicular to the overall interface direction and directed towards the second portion of the wound facing layer.

The present disclosure is based upon the realization that a correct orientation of the wound dressing when initially contacting the wound dressing with the skin of the patient may be used for ensuring that the later removal is performed in a way that reduces the risk of wound damage resulting from the wound dressing removal. That is, when e.g. a nurse or caregiver is to position the wound dressing in relation to the wound, he/she will assess the wound, whereby the removal of the first release sheet will set in which direction the wound dressing will be applied to the skin and consequently, by means of the specifically arranged direction of instruction for removing the wound dressing, the wound dressing should be removed for reducing further wound damage. Accordingly, the orientation of the first release sheet will thus control how the wound dressing is applied by the nurse or caregiver and thus automatically steer how the same or another (future) nurse or caregiver is to and correspondingly will remove the wound dressing.

Thus, an advantage following the wound dressing according to the present disclosure is that the removal direction is correctly and automatically given as soon as the wound dressing has been applied to the wound of the patient. The wound dressing according to the preset disclosure is specifically advantageous in relation to a so called tear wound (also referred to as a skin tear), typically comprising a skin attached portion and a non-attached portion, i.e. a “skin flap” has detached from the patient and must quickly be “reattached” or “reconnected” to ensure wound healing. Accordingly, it will in line with the present disclosure be possible to arrange such that the wound dressing is correctly removed with the skin flap, and not against it, to maintain flap viability. The tear wound is seen as a type of traumatic wound, which typically should proceed to wound closure in a timely fashion.

In accordance to the present disclosure the expression “overall interface direction” should be interpreted broadly, meaning the interface (area) where the first and the second release sheet meet (or are arranged in close vicinity). In line with the present disclosure, the first and the second release sheet must not necessarily each have a “straight” side facing each other at said interface. Rather, the sides facing each other may be slightly rounded (e.g. sinusoidal), jagged or differently arranged. In any case, the overall interface direction will be the “normalized direction” in regards to the sides of the first and the second release sheets where they meet each other.

Preferably, the wound facing layer comprises an adhesive, such as an in comparison low-adhesive, for example comprising a silicone gel, having advantageous features in regards to adhesion as well as during the wound dressing removal process.

Generally, it is preferred that the adhesive is hydrophobic and comprises a substance adapted to adhere to dry skin. Accordingly, the expression “adhere” should be interpreted broadly and mean that the wound dressing should holds its position once applied to the wound. However, the adhesion should at the same time be low enough to reduce the risk of significant disruption or trauma to the wound or to the surrounding skin once the wound dressing is to be removed.

In accordance to the present disclosure the substrate is preferably perforated, e.g. formed from a sheet of non-woven material. A wide range of suitable non-woven materials are commercially available, from a variety of suppliers. Non-woven may for example be produced by extruding polymer fibers to form long thin fibers that may be fused into a web, which has an irregular open structure. It is desirable that the substance used for providing the adhering effect (such as the low-adhesive silicone gel) is arranged at the substrate without closing the perforations of the substrate. Alternatively, the perforated substrate may be a plastic sheet, such as for example formed from polyurethane.

The material and thickness of the substrate is suitably selected to provide backing support to the wound facing layer of the wound dressing, depending on the inherent mechanical strength of the wound facing layer.

Optionally one or more of the parts of the wound dressing may be made in transparent or translucent material. For example, it may assist the nurse or caregiver of the patient suffering from a serious trauma injury to be able to visualize the flows of air and/or fluids into and out of the space above the wound enclosed by the dressing.

The silicone gel that is suitable for use in the present invention will generally be hydrophobic and is preferably tacky. Tacky silicone gels are preferred as they cause the wound dressing to be retained in position when applied, yet are non-adherent. Such silicone gels are of the kind often referred to as soft silicones.

Most preferably, suitable silicone gels are formed by reaction between two components that are mixed to form a silicone gel precursor composition, immediately prior to application to the substrate. Suitable components that are intended for such reaction to form a silicone gel are readily available commercially. Typically, the two components are a vinyl-substituted silicone and a hydride-containing silicone. The precursor composition cures to form the silicone gel. Many such compositions will cure at room temperature, but generally curing is brought about or accelerated by heating.

Gels having different properties may be produced by varying the proportions and/or nature of the components used in the reaction. For example, the molecular weights of the various components and/or their degree of substitution by reactive groups may be different.

Suitable components for forming silicone gels for use in the dressing of the present disclosure are readily available.

In a preferred embodiment of the present disclosure, the first and the second release sheet each comprises a release tab provided at the interface between the first and the second release sheet. Possibly, the first release sheet may be provided with an instruction for removal prior to removing the second release sheet. Furthermore, it may be desirable to arrange the wound dressing such that the tab of the second release sheet is slightly "hidden" below the tab of the first release sheet, whereby it will be more natural for the nurse or caregiver to remove the first release sheet before removing the second release sheet.

In addition, in some embodiments it may be desirable to allow for the first portion of the wound facing layer to be smaller (e.g. as much as 50% smaller) than the second portion of the wound facing layer. Advantageously, this will assist the nurse or caregiver to only have a correspondingly small "tacky portion" to adhere to the skin of the patient. The nurse or caregiver may then successively remove the second release sheet and slowly attach the remaining wound dressing to the patient's skin staring from the interface between the first and the second release sheet.

It should be understood that the first and/or the second release sheet may be subdivided into separate portions. Accordingly, in practice more than just a first and a second release sheet may be comprised with the wound dressing, e.g. depending on the size of the wound dressing. That is, in case of an in comparison large wound dressing it may be desirable to increase the number of release sheets from two to three or even further.

In line with the present disclosure the instruction may for example be printed or dyed at the upper surface of the substrate. That is, it may for example be possible to apply a "screen printing process" (or similar) for forming the printed or dyed, which in some embodiments may be preferred. At the same time, it should be understood that the instruction may be somewhat integrated with the substrate, for example formed at the manufacturing of the substrate.

Generally, the direction of removal of the wound dressing may be formed by an arrow arranged in the removal direction for instructing the nurse or caregiver in what direction to remove the wound dressing. However, it may in some embodiment be desirable to further arrange the instruction in such a manner that e.g. a graphical illustration is provided for further ensuring that the wound dressing is removed starting from the correct end.

According to another aspect of the present disclosure, there is provided a wound treatment method, comprising providing a wound dressing, the wound dressing comprising a substrate having an upper surface and a lower surface, a wound facing layer arranged at the lower surface of the substrate, a first release sheet releasibly covering and protecting a first portion the wound facing layer, and a second release sheet releasibly covering and protecting a second portion of the wound facing layer, wherein the second portion of the wound facing layer is non-overlapping with the first portion of the wound facing layer, wherein an interface between the first and the second release sheet defines an overall interface direction, a printed or dyed instruction comprising a direction of removal of the wound dressing is visibly arranged at an upward facing side of the wound dressing, the upward facing side of the wound dressing arranged at the same side of the substrate as the upper surface of the substrate, and the direction of the removal of the wound dressing is essentially perpendicular to the overall interface direction and directed towards the second portion of the wound facing layer, and applying the wound dressing to a wound of a patient. This aspect of the present disclosure provides similar advantages as discussed above in relation to the previous aspect of the present disclosure.

In line with the discussion above, the wound may for example be a tear wound. Correspondingly, as the tear wound comprises a skin attached portion and a non-attached portion, applying the wound dressing to the wound comprises removing the first release sheet, thereby exposing the first portion of the wound facing layer, contacting, after removing the first release sheet, the first portion of the wound facing layer to the skin attached portion of the skin tear, removing, after contacting the first portion of the wound facing layer, the second release sheet, thereby exposing the second portion of the wound facing layer, and contacting, after removing the second release sheet, the second portion of the wound facing layer at least partly to an unwounded portion of the patients skin in a vicinity of the non-attached portion of the tear wound.

Further features of, and advantages with, the present disclosure will become apparent when studying the appended claims and the following description. The skilled addressee realizes that different features of the present disclosure may be combined to create embodiments other than those described in the following, without departing from the scope of the present disclosure.

BRIEF DESCRIPTION OF THE DRAWINGS

The various aspects of the present disclosure, including its particular features and advantages, will be readily understood from the following detailed description and the accompanying drawings, in which.

DETAILED DESCRIPTION

Figure 1:
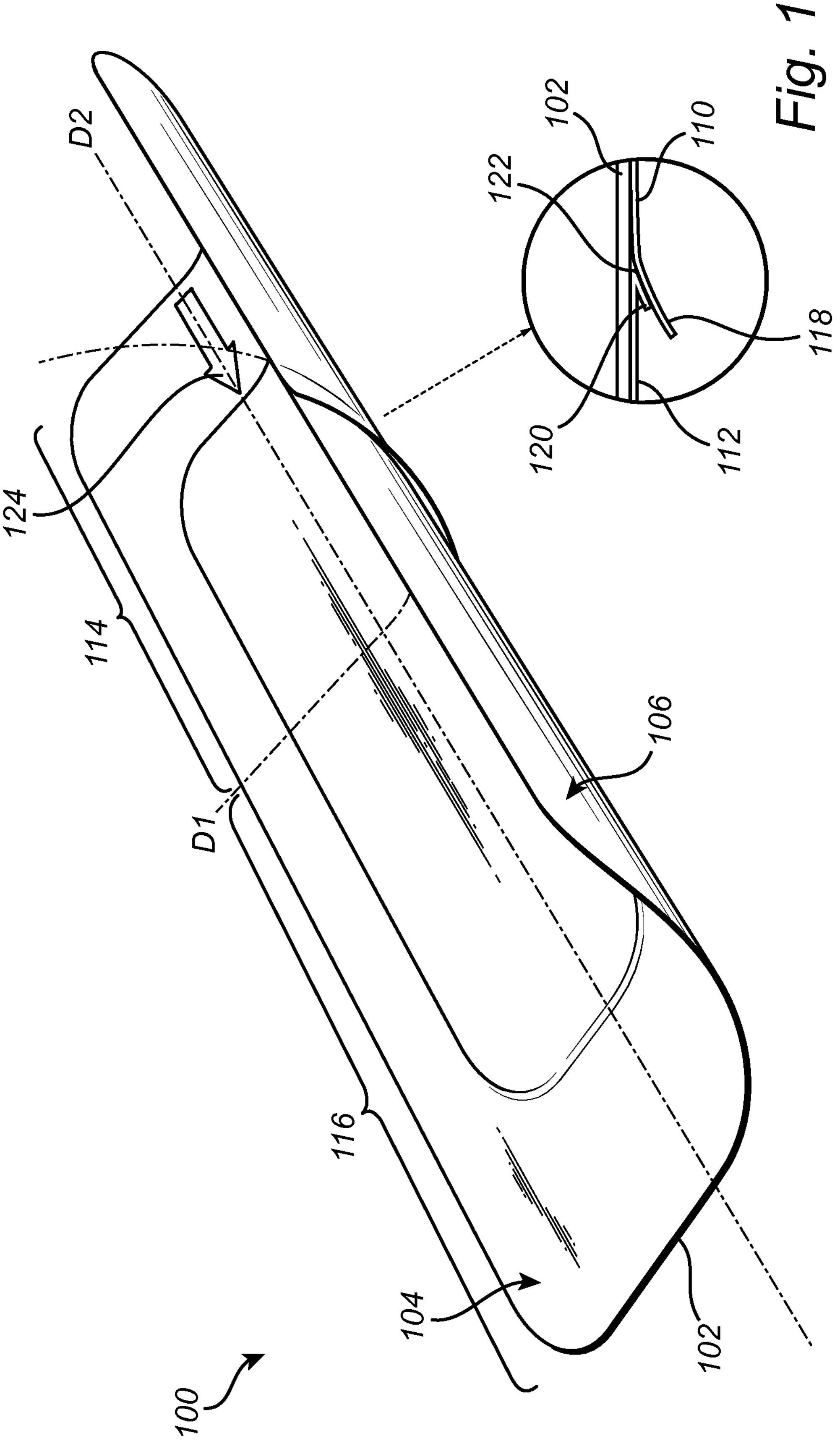
FIG. 1 presents a detailed illustration of an exemplary wound dressing according to an embodiment of the present disclosure.

The present disclosure will now be described more fully hereinafter with reference to the accompanying drawings, in which currently preferred embodiments of the present disclosure are shown. The present disclosure may, however, be embodied in many different forms and should not be construed as limited to the embodiments set forth herein; rather, these embodiments are provided for thoroughness and completeness, and fully convey the scope of the present disclosure to the skilled person. Like reference characters refer to like elements throughout.

Turning now to the drawings and to FIG. 1 in particular, there is provided a wound dressing 100 according to an embodiment of the present disclosure. The wound dressing 100 comprises a substrate 102, the substrate 102 having an upper surface 104 and a lower surface 106. The substrate 102 is preferably perforated, for example formed from a reinforced mesh, a perforated polyurethane film, or a net structure (not explicitly illustrated in FIG. 1).

The wound dressing 100 is typically selected to have a size that correspond to the size of the wound. Accordingly, the size (area of the substrate 102) of the wound dressing 100 may be independently selected in line with the present disclosure. In addition, the wound dressing 100 must not necessarily be of a rectangular shape, but may also be differently formed, such as having a circular or elliptical shape.

The wound dressing 100 further comprises a wound facing layer 108 (not explicitly illustrated in FIG. 1) arranged at the lower surface 106 of the substrate 102, i.e. at the side of the wound dressing 100 that is intended to be placed towards a patient's skin. It is desirable that the wound facing layer 108 is somewhat tacky to ensure that the wound dressing 100 stays at the patient's skin without falling off, e.g. when the patient is moving. The wound facing layer 108 may for example comprise a silicone gel.

The strongly hydrophobic nature of the silicone gel prevents any wound fluid from penetrating out over e.g. healthy skin surrounding the wound and to loosen up skin tissue. The net-like structure of the wound dressing 100 allows for the surrounding, healthy area of the skin to which the dressing is affixed to be maintained airy and rich in oxygen.

The perforated structure of the substrate 102 allows for the passage of excess wound exudate through the wound dressing 100. For the treatment of wounds under regeneration of skin tissue, a dressing according to the present disclosure is preferably combined with an absorbent bandage applied over the wound dressing 100. In this manner excessive amounts of wound exudate will be sucked up at the same time as the absorbent bandage is kept spaced from the wound bed thereby preventing the bandage from sticking to the wound.

To ensure easy handling of the wound dressing 100 at application of the wound dressing 100 to the patient, it is desirable to ensure that the wound facing layer 108 at the lower surface 106 of the wound dressing 100 is covered with a non-tacky element. Specifically, as illustrated in FIG. 1 a first 110 and a second 112 release sheet is respectively arranged to cover and protect a first 114 and a second 116 portion of the wound facing layer 108. As discussed above, it may in some embodiment be desirable to include further release sheets, such as a third release sheet. Such adjustment may for example be desirable in case of in comparison large area wound dressings.

In the illustrated embodiment as shown in FIG. 1 the first portion 114 is arranged to have an essentially corresponding area as the second portion 116. It should however be understood that the areas may be different, such as for example an embodiment where the first portion 114 is in comparison smaller than the second portion 116.

As shown in FIG. 1, the first 110 and the second 112 release sheets are provided with release tabs 118, 120, respectively. In a preferred embodiment, as is shown in FIG. 1, it may be possible to allow the first release tab 118 to slightly "hide" the second release tab 120, thereby making removal of the first tab 118 before the second release tab 120 an intuitive action for the nurse or caregiver when applying the wound dressing to the patient.

As also shown in FIG. 1, the first portion 114 and the second portion 116 have one side facing each other, forming an interface 122 between the first and 114 and the second 116 portion. In the illustrated embodiment, the interface is essentially straight, meaning that the sides of the first 114 and the second 116 portion facing each other are equally straight. However, the interface 122 may be slightly "wavy" or "jagged". In any case, an overall direction D1 of the interface 122 essentially "cuts through" the essentially rectangular wound dressing 100, seen as a normalized direction in case of the interface being wavy or jagged.

Correspondingly, the upper surface 104 of the wound dressing 100 is provided with a printed or dyed instruction 124 comprising a direction D2 of removal of the wound dressing 100. The printed or dyed instruction 124 is arranged to be visible at an upward facing side of the wound dressing 100, i.e. in the direction facing away from the patent skin when the wound dressing 100 has been applied thereto. The instruction 124 may be "integrated" with the substrate 102 or provided at the upper surface 104, such as e.g. by screen printing or any other present or future printing or dying method.

As is illustrated in FIG. 1 the direction of the removal D2 of the wound dressing 100 is essentially perpendicular to the overall interface direction D1 and additionally directed, starting from the first portion 114, towards the second portion 116 of the wound facing layer 108. That is, the intended direction of removal D2 of the wound dressing 100 is to start with the first portion 114 of the wound dressing 100 and then to continue with the second portion 116 of the wound dressing 100 until the wound dressing 100 has been completely removed, as will be further elaborated below.

Figure 2A:
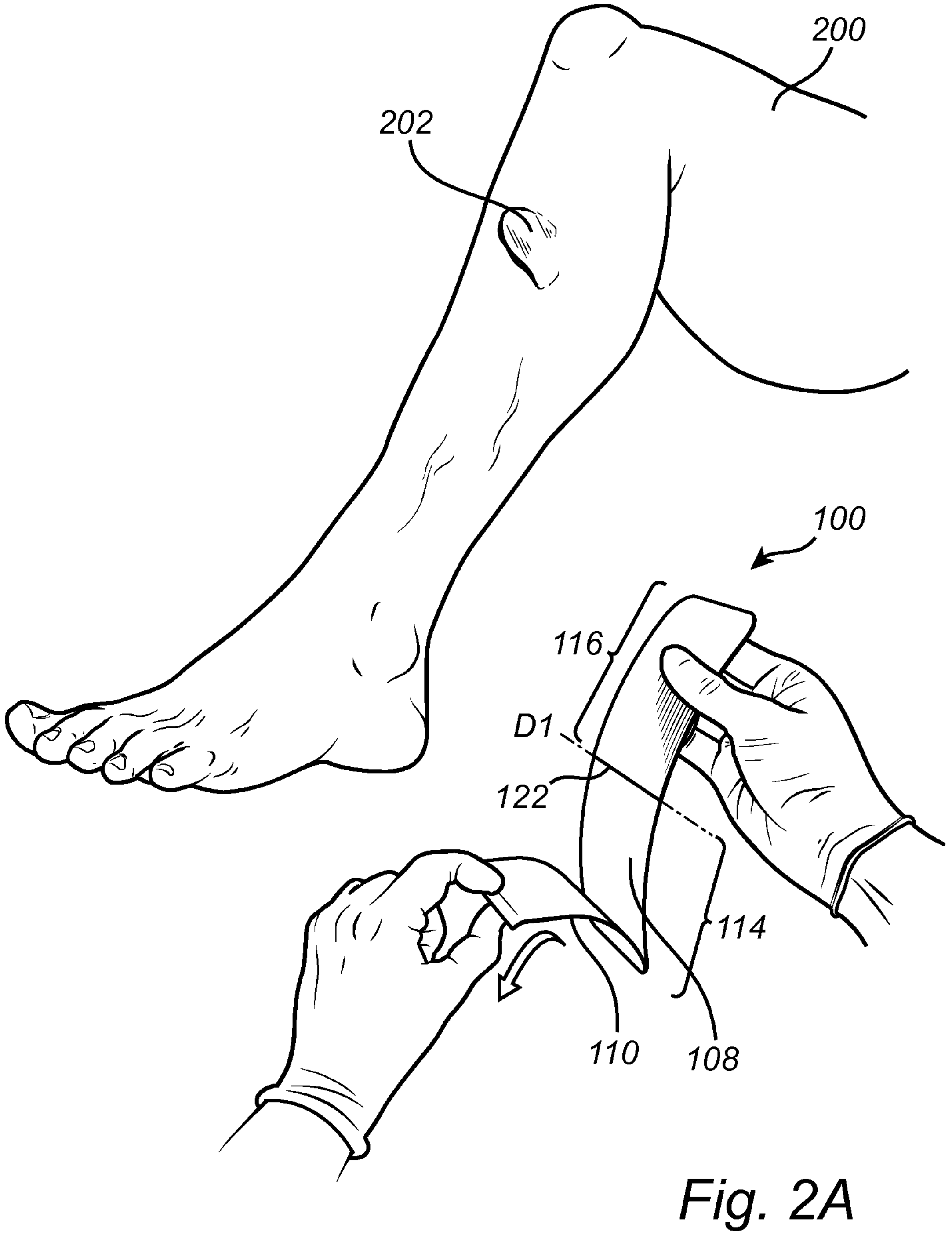
FIGS. 2A-2D shows an attachment and removal procedure of a wound dressing according to the present disclosure.
Figure 2B:
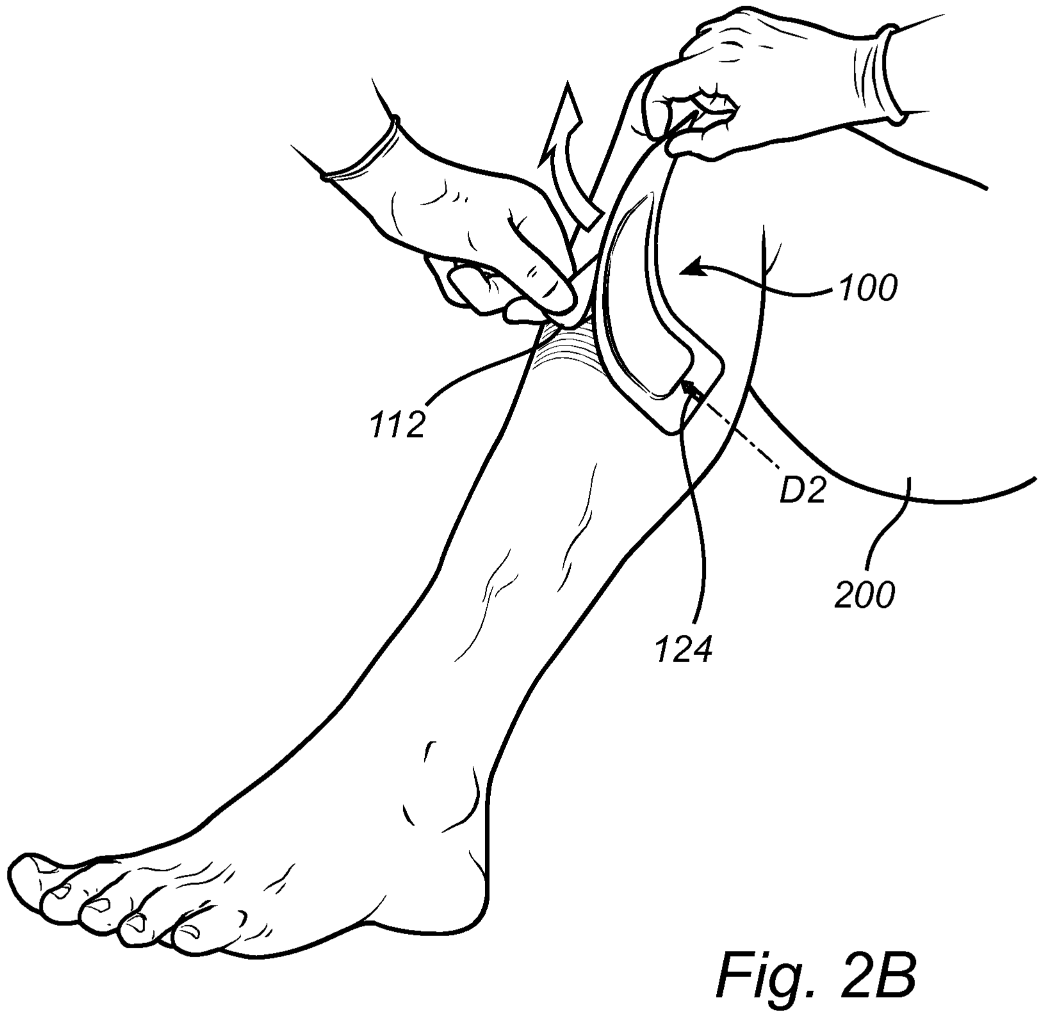
Figure 2C:
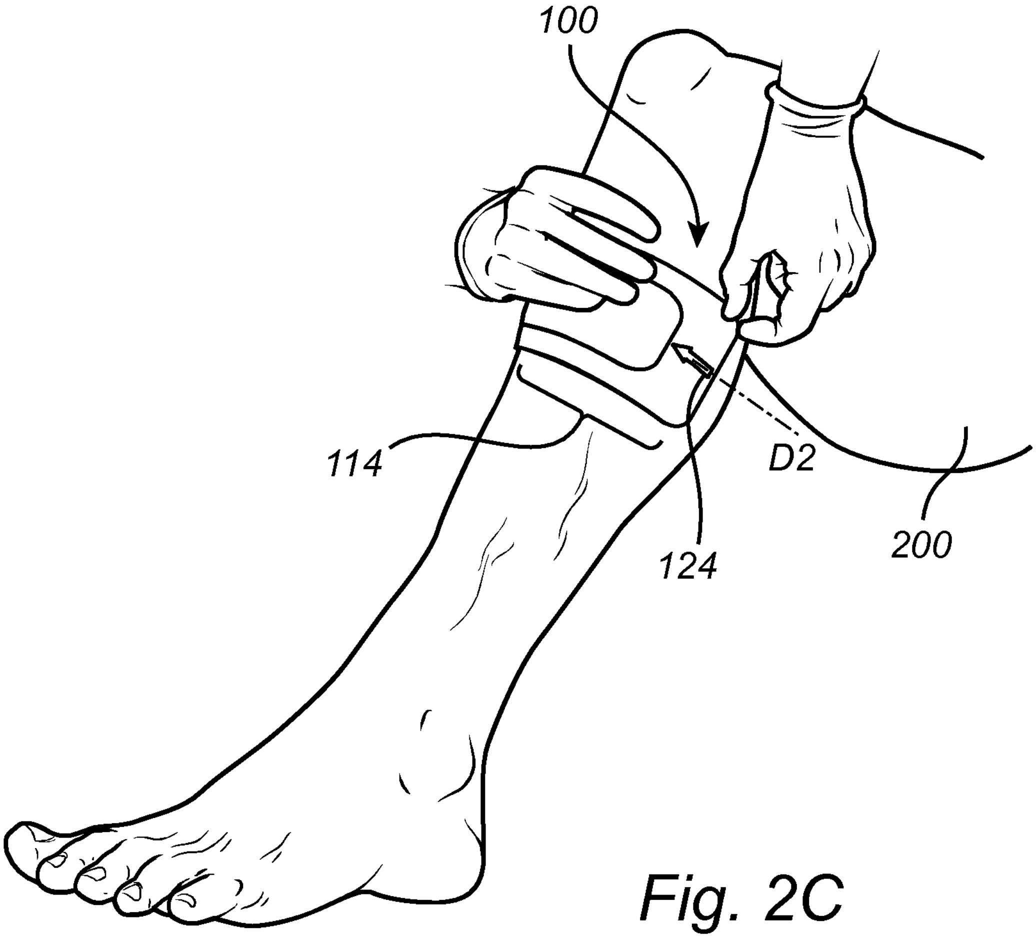
Figure 2D:
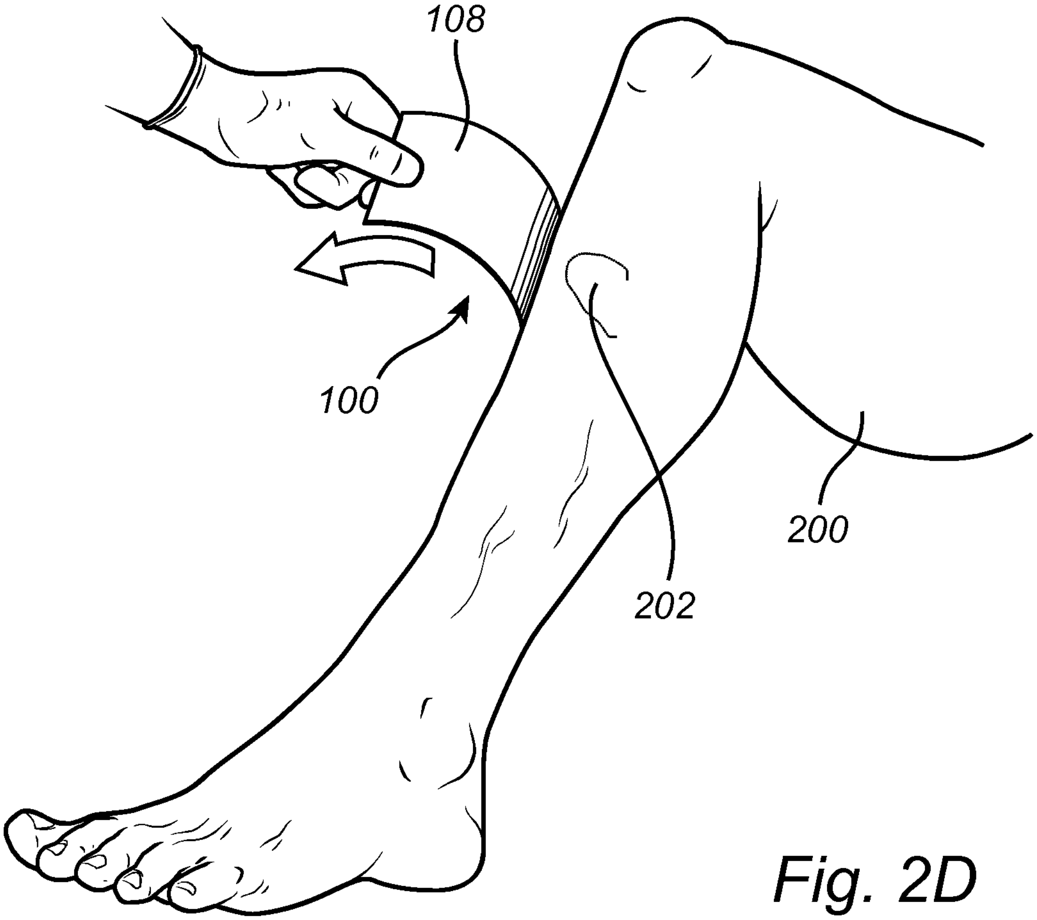
Figure 3:
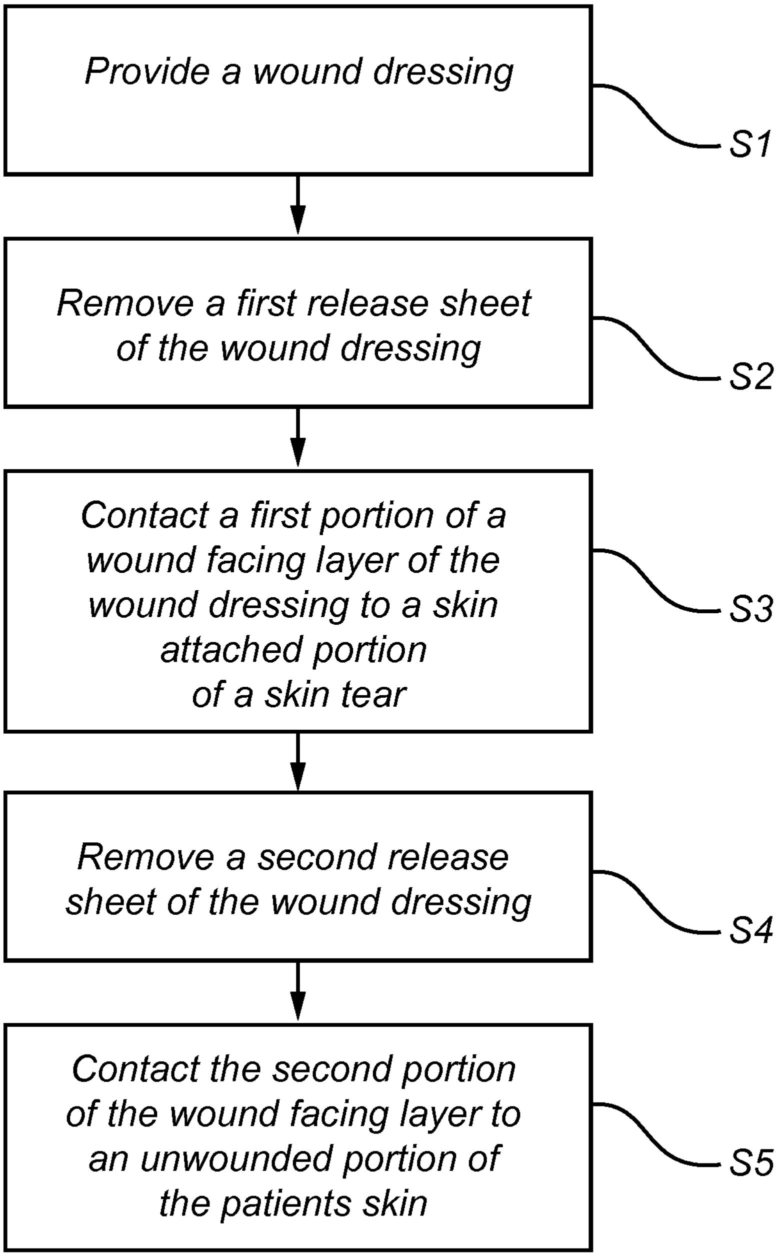
FIG. 3 is a flow chart for applying the wound dressing to a patent in line with the present disclosure.

Turning now to FIGS. 2A-2D in conjunction with FIG. 3, where it is illustrated an attachment and removal procedure of the wound dressing 100 to a patient 200. In FIG. 2A it is illustrated a lower part of a leg of the patient 200. As is shown, the patient has a so-called tear wound 202 (also referred to as a skin tear). A tear wound may for example be caused by shear, friction, and/or blunt force resulting in separation of skin layers, and may be partial-thickness (separation of the epidermis from the dermis) or full-thickness (separation of both the epidermis and dermis from underlying structures).

Generally, tear wounds are traumatic wounds, which have a high probability of becoming complex chronic wounds, if not properly managed. As is known by the skilled person, the tear wound comprises a "skin attached portion" and a "non-attached portion" (e.g. comprising a so called skin flap), where the non-attached portion is the "loose" portion of the tear wound that is desirable to be "reattached". It is, as understood from the above, desirable to always remove the wound dressing 100 with the skin flap, and not against it, to maintain flap viability, i.e. starting from the skin attached portion.

To protect the tear wound 202 and reduce the risk of future complications it is desirable to quickly attach a wound dressing, such as wound dressing 100, typically following a wound cleansing process and an approximation of wound edges. Accordingly, in line with the present disclosure the wound dressing 100 is provided, where the wound dressing 100 is formed in line with the discussion as provided above.

As shown in FIG. 2A, the nurse or caregiver has optionally performed the wound cleansing process and the approximation of wound edges, and is attaching the wound dressing 100 to the tear wound 202 of the patient 200 by first removing the first release sheet 110 (typically starting at the interface 122 using the release tab 118), thereby exposing the first portion 114 of the wound facing layer 108. As then shown in FIG. 2B, the tacky surface of the first portion 114 of the wound facing layer 108 is then contacted, S2, with the to a skin attached portion of the skin tear 202.

Once the first portion 114 has been correctly contacted to the patient's skin, the nurse or caregiver will remove, S3, the second release sheet 112, thereby exposing the second portion 116 of the wound facing layer 108 and consequently contact, S4, the second portion 116 of the wound facing layer 108 at least partly to an unwounded portion of the patient's skin in a vicinity of the non-attached portion of the tear wound 202.

Once the wound dressing 100 has been correctly attached to the patient 200 in relation to the "direction" of the tear wound 202, i.e. in relation to the attached and the non-attached portion of the tear wound 202, also the intended direction of removal D2 of the wound dressing 100 will be correct.

That is, by arranging the release sheets 110, 112 in the manner as defined by the present disclosure it is possible to also reduce the risks that the wound dressing 100 erroneously removed, which would be the case if the nurse or caregiver wound start by removing the second portion 116 of the wound dressing 100. However, in line with the present disclosure the nurse or caregiver will automatically be provided with a correct instruction regarding the direction for removal D2 of the wound dressing 100, ensuring that the nurse or caregiver will start with the first portion 114 of the wound dressing 100.

As shown in FIG. 2C, the instruction of direction for removal D2 of the wound dressing 100 is visibly shown to the nurse or caregiver, meaning that the removal instruction of arranged to face upwards regarding the wound dressing 100, the upward facing side of the wound dressing arranged at the same side of the substrate 102 as the upper surface 104 of the substrate 102.

In FIG. 2D the wound dressing 100 has been completely removed, illustrating how the tear wound 202 has been at least partly healed.

It should be understood that the wound dressing according to the present disclosure may be used for human or animal use.

Although the figures may show a sequence the order of the steps may differ from what is depicted. Also, two or more steps may be performed concurrently or with partial concurrence. Such variation will depend on the systems chosen and on designer choice. All such variations are within the scope of the disclosure.

Additionally, even though the present disclosure has been described with reference to specific exemplifying embodiments thereof, many different alterations, modifications and the like will become apparent for those skilled in the art.

In addition, variations to the disclosed embodiments can be understood and effected by the skilled addressee in practicing the present disclosure, from a study of the drawings, the disclosure, and the appended claims.

Furthermore, in the claims, the word "comprising" does not exclude other elements or steps, and the indefinite article "a" or "an" does not exclude a plurality.

Furthermore, in the foregoing description, various embodiments have been presented for the purpose of illustration and description. They are not intended to be exhaustive or to limit the disclosure to the precise forms disclosed. Obvious modifications or variations are possible in light of the above teachings.

The embodiments were chosen and described to provide the best illustration of the principals of the present disclosure and its practical application, and to enable one of ordinary skill in the art to utilize the various embodiments with various modifications as are suited to the particular use contemplated.

All such modifications and variations are within the scope of the present disclosure as determined by the appended claims when interpreted in accordance with the breadth they are fairly, legally, and equitably entitled.

The invention claimed is:

1. A wound dressing, comprising:

a substrate having an upper surface and a lower surface, wherein the substrate defines a lateral axis and a longitudinal axis transverse to the lateral axis;

a wound facing layer comprising an adhesive arranged at the lower surface of the substrate;

a first release sheet releasably covering and protecting a first portion of the wound facing layer, wherein the first release sheet comprises a first release tab; and a second release sheet releasably covering and protecting a second portion of the wound facing layer, wherein the second portion of the wound facing layer is non-overlapping with the first portion of the wound facing layer, wherein the second release sheet comprises a second release tab, wherein:

an interface between the first and the second release sheet defines an overall interface direction along the lateral axis;

wherein the first release tab is arranged to hide the second release tab such that during use the first release sheet is removed prior to the second release sheet by use of the first release tab;

a printed or dyed instruction comprising a direction of removal of the wound dressing is visibly arranged at an upward facing side of the wound dressing, the upward facing side of the wound dressing arranged at the same side of the substrate as the upper surface of the substrate, wherein the printed or dyed instruction is provided on a portion of the upward facing side of the wound dressing that overlies the first portion; and the direction of the removal of the wound dressing is essentially perpendicular to the lateral axis and directed towards the second portion of the wound facing layer along the longitudinal axis.

2. The wound dressing according to claim 1, wherein the substrate comprises a reinforcing component.

3. The wound dressing according to claim 2, wherein the reinforcing component comprises a flexible and elastically-extendable textile material.

4. The wound dressing according to claim 3, wherein the textile material is a knitted textile.

5. The wound dressing according to claim 1, wherein the first release tab and the second release tab are provided at the interface between the first and the second release sheet.

6. The wound dressing of claim 5, wherein the second release tab is positioned between the second release sheet and the first release tab.

7. The wound dressing according to claim 1, wherein the first portion of the wound facing layer is smaller than the second portion of the wound facing layer.

8. The wound dressing according to claim 7, wherein the first release sheet is provided with an instruction for removal prior to removing the second release sheet.

9. The wound dressing according to claim 1, wherein the substrate comprises a perforated plastic sheet.

10. The wound dressing according to claim 9, wherein the perforated plastic sheet is formed from polyurethane.

11. The wound dressing according to claim 1, wherein the adhesive comprises a silicone gel.

12. The wound dressing according to claim 1, wherein the adhesive is hydrophobic and comprises a substance adapted to adhere to dry skin.

13. The wound dressing according to claim 1, wherein the substrate is hydrophobic.

14. The wound dressing of claim 1, wherein the printed or dyed instruction includes an arrow indicating the direction of removal of the wound dressing.

15. The wound dressing of claim 1, wherein the direction of removal is oriented toward the interface.

16. The wound dressing of claim 1, wherein the direction of removal is oriented toward a central portion of the wound dressing.

17. The wound dressing of claim 1, wherein the interface is non-linear.

* * * * *